United States Patent [19]

Tower

[11] Patent Number: 5,389,106
[45] Date of Patent: Feb. 14, 1995

[54] IMPERMEABLE EXPANDABLE INTRAVASCULAR STENT

[75] Inventor: Allen J. Tower, North Lawrence, N.Y.

[73] Assignee: Numed, Inc., Nicholville, N.Y.

[21] Appl. No.: 145,435

[22] Filed: Oct. 29, 1993

[51] Int. Cl.6 .......................................... A61M 29/00
[52] U.S. Cl. ........................................ 606/198; 623/1; 623/12
[58] Field of Search ........ 606/198, 200, 108, 191–194; 623/1, 12

[56] References Cited

U.S. PATENT DOCUMENTS

| | | |
|---|---|---|
| 4,313,231 | 2/1982 | Koyamada . |
| 4,503,569 | 2/1985 | Dotter . |
| 4,617,332 | 10/1986 | Salyer et al. . |
| 4,733,665 | 3/1988 | Palmaz . |
| 4,739,762 | 4/1988 | Palmaz . |
| 4,776,337 | 10/1988 | Palmaz . |
| 4,793,348 | 12/1988 | Palmaz . |
| 4,820,298 | 4/1989 | Leveen et al. . |
| 4,830,003 | 5/1989 | Wolff et al. . |
| 4,856,516 | 8/1989 | Hillstead . |
| 4,886,062 | 12/1989 | Wiktor . |
| 5,116,365 | 5/1992 | Hillstead ............................ 623/1 |
| 5,122,154 | 6/1992 | Rhodes ............................. 606/198 |
| 5,123,917 | 6/1992 | Lee .................................. 623/1 |
| 5,217,483 | 6/1993 | Tower . |

OTHER PUBLICATIONS

Arizona Heart Institute Foundation, *A View of Vascular Stents*, Richards A. Schatz, M.D. (Oct. 7, 1988).

Primary Examiner—Stephen C. Pellegrino
Assistant Examiner—William W. Lewis
Attorney, Agent, or Firm—Harris Beach & Wilcox

[57] ABSTRACT

There is disclosed a radially expandable stent for intravascular implantation comprising a distensible frame and an impermeable deformable membrane interconnecting portions of the frame to form an impermeable exterior wall. The membrane is formed of a synthetic non-latex, non-vinyl polymer, and the frame comprises a fine wire of annealed platinum. The comprises a plurality of helically aligned circumferential sections including two end sections and a plurality of intermediate sections that define a cylinder having a longitudinal axis, the cylinder being formed of a continuous wire with the circumferential sections being spaced along the axis in abutting contact. Each of the circumferential sections have expandable segments that impart radial expandability to the sections. The expandable segments are tear-drop shaped elements that are alternately inverted about the circumferential sections, each element containing a base and a pair of legs that come together at a common apex when the stent is in an unexpanded condition. One of the end sections has a pigtail that is passed back along the circumferential sections and is joined to the other end section to prevent axial expansion of the expanded during radial expansion.

5 Claims, 2 Drawing Sheets

IMPERMEABLE EXPANDABLE INTRAVASCULAR STENT

BACKGROUND OF THE INVENTION

1. Field of the Invention

This invention relates to intravascular implants for maintaining vascular patency in human blood vessels. More particularly, this invention relates to a radially expandable stent made from a fine wire formed into a serpentine ribbon wound into a cylindrical shape for introduction into a body vessel for balloon expansion therein in a radial fashion to support the wall of the vessel when in the expanded configuration. The stent includes an impermeable membrane that lies in the plane of the cylinder. This invention is particularly useful in transluminal implantation of a stent for use in the coronary angioplasty to prevent restenosis, and for the treatment of aneurysms or subintimal dissections.

2. Description of the Prior Art

The basic concept of stents has been known for a number of years. Various types of stents have been proposed and patented, including self-expanding spring types, compressed spring types, mechanically actuated expandable devices, heat actuated expandable devices, and the like. More recently, expandable sleeves have been proposed such as shown in Palmaz, U.S. Pat. No. 4,733,665. In this disclosure there is shown a sleeve having slots therethrough to form a permeable mesh. The sleeve is placed transluminally, and then expanded by a balloon catheter through the elastic limit of the metal so as to permanently deform the sleeve into supporting contact with the interior surface of a blood vessel. Other examples of expandable wire stents are shown in Hillstead, U.S. Pat. No. 4,865,516, and Wiktor, U.S. Pat. No. 4,886,062.

In my U.S. Pat. No. 5,217,483 (referred to hereinafter as the '483 Patent) I disclose the use of a fine platinum wire bent into a serpentine flat ribbon which is wound around a mandrel into a radially expandable cylindrical sleeve for mounting on a balloon catheter for transluminal intravascular placement. The expanded sleeve as disposed in a vessel possesses gaps or interstices which are believed to protect the vascular endothelium from contact therewith, and to promote endothelial proliferation and remodeling of the vascular intima about the sleeve. However in many cases the trauma of implantation causes microscopic or even macroscopic intimal tears, and exposes the subintimal space to the bloodstream. This is undesirable as further dissection of the vessel is possible. Furthermore tissue reactions, including thrombus formation, intimal fibroplasia, and cicatrization could result in restenosis of the vessel.

Permeable transluminally placed intravascular stents are suboptimum for the treatment of aneurysms. While the structure of the expanded mesh may reduce the pulsatile forces acting against a weakened arterial wall, this effect is doubtless incomplete. The art has long utilized grossly impermeable continuous structures such as Teflon grafts and implants for aneurysm repair in larger vessels by conventional open surgical techniques.

SUMMARY OF THE INVENTION

It is an object of the present invention to provide an improved expandable stent adapted to percutaneous intravascular implantation for supporting the wall of a blood vessel and for stabilizing an aneurysm thereof.

It is another object of the present invention to provide an improved intravascular stent that reduces the rate of restenosis in a vessel subjected to angioplasty therewith.

It is yet another object of the present invention to provide an improved expandable stent that can be percutaneously implanted in a vessel without injury to the vessel.

These and other objects of the present invention are attained by a radially expandable stent for intravascular implantation comprising a distensible frame and an impermeable deformable membrane interconnecting portions of the frame to form an impermeable exterior wall. The tubular member is dimensioned to receive an inflatable catheter for intravascular placement and radial expansion therewith. Expansion of the catheter and the stent brings the wall surface into supporting contact with an interior surface of a vessel.

The membrane is formed of a synthetic non-latex, non-vinyl polymer, and the frame comprises a fine wire of annealed platinum.

According to one aspect of the invention, the membrane extends from end to end of the frame.

In another aspect of the invention the membrane is disposed on the central portion of the frame, and at least one of the frame ends are not covered by or in contact with the membrane in order to permit anchoring of the ends to the vessel once tissue reaction or remodeling of the vessel wall has occurred about the ends of the stent.

In a preferred embodiment the radially expandable stent comprises a plurality of helically aligned circumferential sections including two end sections and a plurality of intermediate sections that define a cylinder having a longitudinal axis, the cylinder being formed of a continuous wire with the circumferential sections being spaced along the axis in abutting contact. Each of the circumferential sections have expandable segments that impart radial expandability to the sections, whereby the sections have an unexpanded insertion circumference and an expanded implantation circumference that is greater than the insertion circumference. The expandable segments are tear-drop shaped elements that are alternately inverted about the circumferential sections, each element containing a base and a pair of legs that come together at a common apex when the stent is in an unexpanded condition. One of the end sections has a free end or pigtail that is passed back along the circumferential sections and is joined to the other end section to prevent axial expansion of the stent during radial expansion. The elements and the circumferential segments are interconnected by a distensible impermeable membrane formed of a synthetic non-latex, non-vinyl polymer to define a exterior wall surface that contacts an interior surface of a vessel upon radial expansion of the stent.

In accordance with an aspect of the invention the membrane is attached to the frame by placing the frame on a mandrel; providing a solution of the polymer in an organic solvent such as toluene; dipping the frame and the mandrel into the solution; withdrawing the frame and the mandrel from the solution; thereafter drying the frame and the mandrel; and finally removing the mandrel from the frame. The steps of dipping and drying are preferably performed at room temperature.

BRIEF DESCRIPTION OF THE DRAWING

For a better understanding of these and other objects of the present invention, reference is made to the detailed description of the invention which is to be read in conjunction with the following drawings, wherein.

DESCRIPTION OF THE PREFERRED EMBODIMENT

Figure 1:
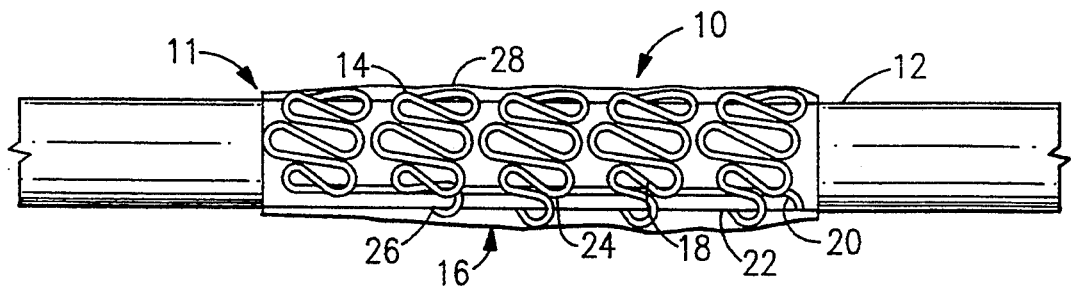
FIG. 1 is a side elevation of an unexpanded stent in accordance with the invention supported on a mandrel.
Figure 2:
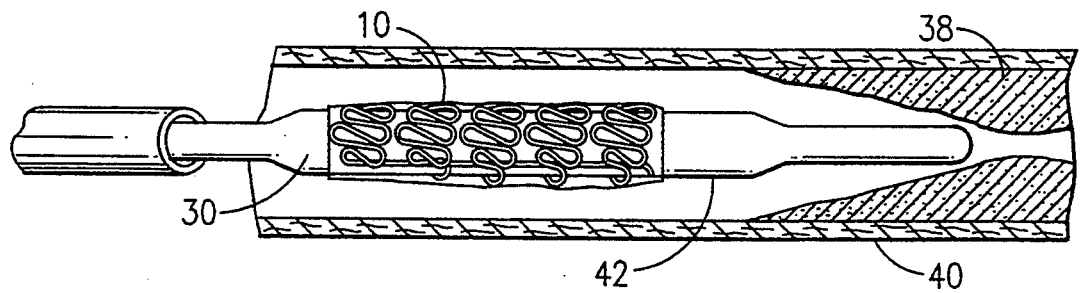
FIG. 2 is a view similar to FIG. 1 showing the stent mounted about a collapsed balloon catheter inserted in a blood vessel.

Turning now to the Drawing, there is shown in FIG. 1 a stent 10 in accordance with the present invention carried on a mandrel 12 during manufacture. As taught in the '483 Patent, a wire frame or sleeve 11 of the stent is formed by first taking a fine wire 14 having a diameter of approximately 0.004", preferably made from platinum, and forming it into a generally sinusoidal form, in which approximately ten cycles or segments per inch are formed in the wire. These bends can be formed in any convenient manner, for instance as by bending about a rack gear by running a corresponding spur gear over a wire laid along the rack. The next step is to take the wire 14 and to further bend it into a serpentine or figure eight configuration so that the edges of each loop touch and abut the adjacent edges of the next loop forming the tight-looped serpentine ribbon form 16. In this configuration, approximately forty loops per inch of ribbon are present and the height or "amplitude" of the loops is approximately 1/16". This is accomplished by mechanically bending the partially formed loops 18, 18 up against each other into the tear-drop shapes shown in FIG. 1. The fine wire 14 used to form the basic flat ribbon 16 is a soft platinum wire that has been fully annealed to remove as much spring memory as possible. The straight wire before bending, being in the fully annealed condition, retains whatever shape it is formed into. After the flat narrow serpentine ribbon 16 is formed, it is wrapped about a mandrel 12 having a diameter of 0.060" in a spiral or helix fashion with the edges of each helix wrap of the ribbon 16 basically touching the adjacent ribbon helix edges to form the wire sleeve 11. The number of convolutions of the helix on the mandrel determines the length of the sleeve 11, and a typical stent of this type may have a length of approximately one and one-half inches. As the serpentine ribbon 16 of FIG. 2 is wound on the mandrel 12, the pigtail 20 of the wire 14 is inserted through the helix, as may be seen in FIG. 1. In actual practice, the ribbon 16 is wound about the mandrel 12 over top of the pigtail 20 of the wire 14. After the helix is formed to the desired length, the free end of the pigtail 20 extending through the helix is trimmed and welded smoothly to the final turn of the helix so as not to present any increased profile, and so as not to puncture or pierce the balloon catheter or the blood vessel into which it is being inserted. The end turn of the helix is welded at 22 and intermediate welds such as 24 are formed to stabilize the length of the helix. The first turn of the helix at the other end may also be welded to the pigtail at 26 so that the overall length of the stent can be constrained and maintained in the desired configuration.

After formation of the wire sleeve 11, a synthetic polymer membrane 28 is bonded to the sleeve 11 to form an impermeable wall or barrier. The membrane 28 should be a hypoallergenic, biologically inert material, that is free of latex rubber proteins and processing chemicals that can cause adverse reactions. The material is preferably Tactylon®, available from Tactyl Technologies, Inc., of Vista, Calif. Tactylon is well known to have properties of elasticity, distensibility and barrier protection without the sensitization problems associated with natural rubber.

The attachment of the polymer membrane 28 to the sleeve 11 is accomplished by dipping the sleeve 11 and the mandrel 12 into a solution of Tactylon in an organic solvent such as toluene at room temperature. The solution permeates the wire sleeve 11, coating the wires thereof. The sleeve 11 and mandrel 12 are then withdrawn from the solution and allowed to dry at room temperature. During drying the polymer forms a membrane 28 that spans the interstices of the sleeve 11, and the result is a continuous impermeable membranous wall that incorporates the wire sleeve 11 and covers the gaps and interstices in the sleeve's ribbon and helical substructures. The presence of the mandrel 12 during the development of the membranous wall assures that the lumen of the sleeve 11 remains patent, and that the ends of the sleeve 11 remain open. When the mandrel 12 is removed, the final stent 10 is an impermeable wire-reinforced tube or cylinder which is open at each end.

Figure 3:
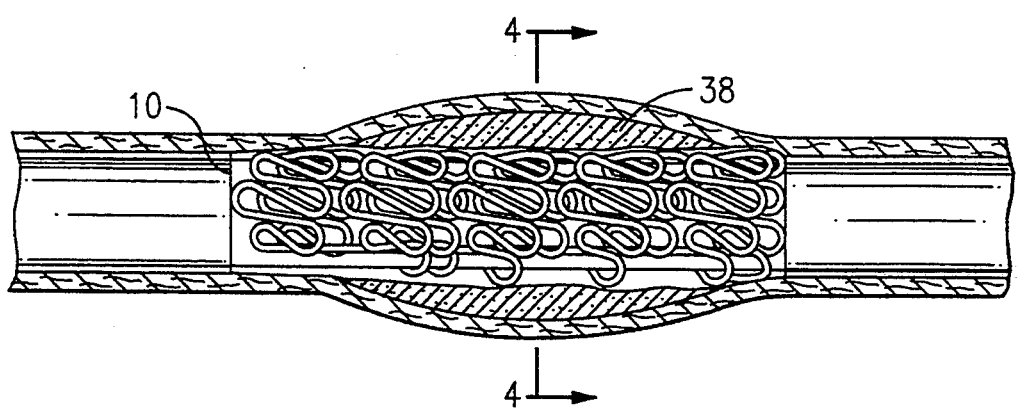
FIG. 3 is a view similar to FIG. 3 on a reduced scale showing the expanded stent in position in a blood vessel for holding the blood vessel in an open configuration.

The stent 10 is used by placing it about the inflatable distal portion of a conventional collapsed balloon catheter 30 as shown in FIG. 2. In this configuration, the sleeve 11 generally has a diameter in the neighborhood of 1.5 mm for insertion into the coronary arteries. In a known manner the balloon catheter 30 with the stent 10 mounted thereon is inserted into the appropriate blood vessel 40. The stent 10 is guided to the desired location where there is an occluding plaque 38 or an aneurysm or other imperfection requiring placement of a stent. As the stent is passed through a stenotic segment of the vessel 40, the membrane 28 presents a smooth surface that gently glides along the intima 42 of the vessel 40, and is unlikely to abrade the endothelium, or create small intimal tears, or otherwise traumatize the plaque 38 so as to produce intramural hemorrhage. Once the stent 10 is properly located and verified by fluoroscopic or other technique, the balloon catheter 30 is inflated to radially expand the serpentine wire sleeve 11. As the balloon expands, it expands the tight tear drop bends of the serpentine ribbon 16 as explained in detail in the '483 Patent. For instance, in a particular embodiment where the diameter of the stent on the collapsed balloon catheter was 1.5 mm, the stent 10 has been expanded to 4–5 mm within the blood vessel 40 as shown in FIG. 3. The expanded stent maintains good interior surface support of the blood vessel by maintaining the close spacing of the wire loops and helices forming the sleeve. The reinforced impermeable membranous wall 28 is believed to attenuate the pulsatile hydraulic forces that are experienced by the segment of the blood vessel 40 in contact therewith and thereby prevent the enlargement or rupture of an aneurysm. The stent 10 is thus particularly suitable for the mechanical stabilization of vascular aneurysms.

Figure 4:
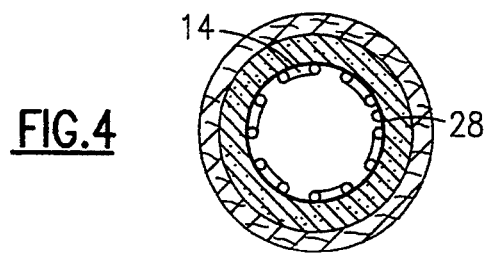
FIG. 4 is a sectional view through line 4—4 of FIG. 3.

The expanded condition of the stent is shown in FIGS. 3 and 4 with the balloon catheter 30 having been removed. The stenotic segment is now dilated and the lumen of the vessel 40 is enlarged. In a case where the abnormal segment of the vessel 40 has an aneurysm, it is believed that the impermeable membrane 28 as reinforced by the wire sleeve 11 can prevent the dislodgement and subsequent embolization of fragments of plaque and thrombus that sometimes form in aneurysms. Also since the wire pigtail has no sharp ends and the free end is welded to the loop of the helix, there are no sharp edges or points to tear or catch on the catheter balloon or the interior surface of the blood vessel. Thus the stent of the present invention can be readily manipulated to the desired location. In prior art devices where the necessary surface support had to be achieved by heavier wire or a denser sleeve, it became difficult to flex the sleeve so as to transit the convoluted blood vessels. When a looser wire configuration was employed, the stability of the stent was decreased and the ultimate efficacy of the implanted stent compromised.

Figure 5:
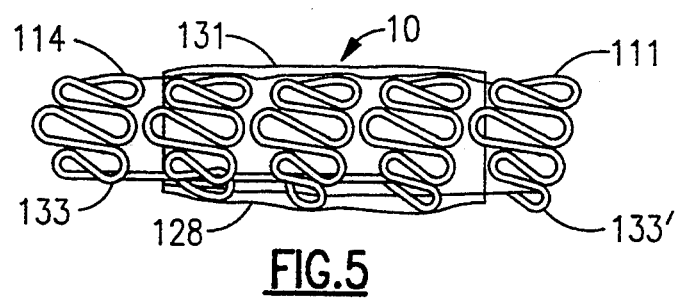
FIG. 5 is a side elevation similar to FIG. 1 of an unexpanded stent in accordance with an alternate embodiment of the invention.
Figure 6:
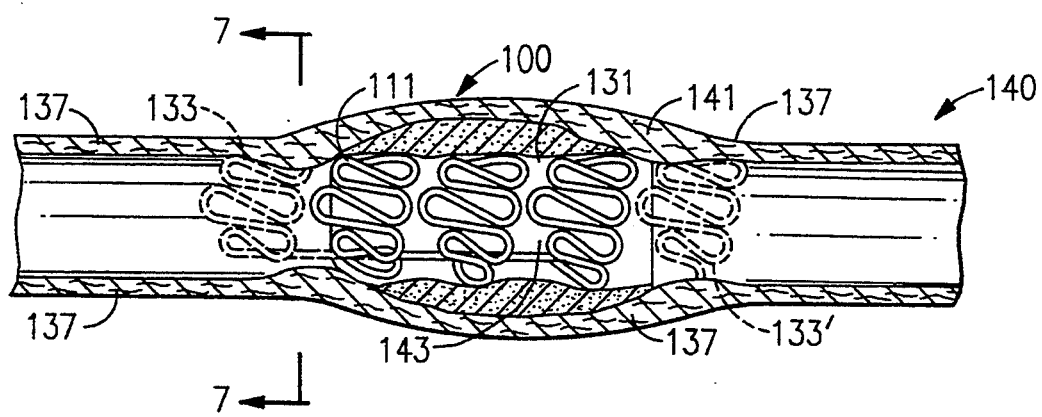
FIG. 6 is a sectional view of a diseased blood vessel illustrating the stent of FIG. 5 expanded therein.
Figure 7:
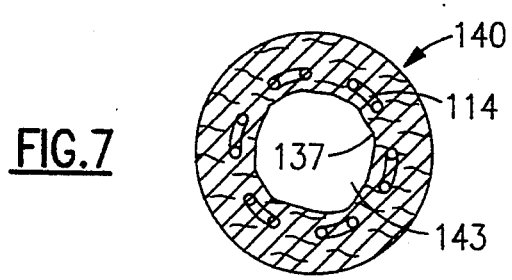
FIG. 7 is a sectional view through line 7—7 of FIG. 6.

Turning now to FIGS. 5 and 6, there is shown an alternate embodiment of a stent 110 in accordance with the invention. In FIG. 5 an unexpanded stent 110 is similar to the first embodiment, except now the membrane 128 only forms a wall of a central portion 131 of a wire sleeve 111, and does not extend to end portions 133, 133'. In FIG. 6 there is shown the stent 110 which has been conventionally implanted in a diseased blood vessel 140, and has been in place for a sufficient period for tissue reaction to occur. The diseased portion of the vessel 140 is shown as an enlarged segment 141, the diseased condition typically being an aneurysm with a mural thrombus, or a plaque that has now been dilated by the radially expanded stent 110. The impermeable membrane 128, reinforced by the wire sleeve 111, is in sealing and stabilizing contact with the intimal surface of the diseased segment 141, and the lumen 143 of the stent 110 is patent, allowing free flow of blood therethrough. In the end portions 133, 133' there are open interstices of the wire sleeve 111, so that contact between the stent 110 and the intimal surface of the vessel 140 is limited to the wire 114. This allows a tissue reaction (shown as dark areas 137, 137) to develop about the end portions 133, 133', and firmly incorporate the end portions 133, 133' of the stent 110 into the wall of the blood vessel 140.

The stent 110 is manufactured in much the same way as that of the first embodiment. It is necessary, however to shield the end portions 133, 133' from contact with the non-latex polymer solution. This can be accomplished mechanically by a folded protective sheath or similar. The sheath is removed with the mandrel after drying.

It will be understood that the benefits of the impermeable membrane are not limited to the particular frame embodiments disclosed herein. The membrane can be applied to other frame constructions that are known to the art.

While this invention has been explained with reference to the structure disclosed herein, it is not confined to the details set forth and this application is intended to cover any modifications and changes as may come within the scope of the following claims:

What is claimed is:

1. A radially expandable stent for intravascular implantation comprising:

a tubular structure having a longitudinal axis, a radius, a central portion, and first and second ends, said tubular structure comprising a distensible frame and an impermeable distensible membrane interconnecting portions of said frame to form an impermeable wall surface disposed between said first and second ends about said axis, said tubular structure being adapted to receive an inflatable catheter for intra vascular placement and radial expansion therewith, wherein said membrane is disposed on said central portion and at least one of said first end and said second end is not in contact with said membrane;

whereby expansion of said catheter and said tubular structure brings said wall surface into supporting contact with an interior surface of a vessel.

2. The stent in accordance with claim 1, wherein said membrane comprises a synthetic non-latex, non-vinyl polymer.

3. The stent in accordance with claim 1, wherein said frame comprises a fine wire.

4. The stent in accordance with claim 1, wherein said membrane extends from said first end to said second end.

5. The stent in accordance with claim 1, wherein neither said first end nor said second end is in contact with said membrane.

* * * * *